(12) United States Patent
Sakaguchi (10) Patent No.: US 9,629,758 B2
(45) Date of Patent: Apr. 25, 2017

(54) DISPOSABLE DIAPER

(71) Applicant: UNICHARM CORPORATION, Shikokuchuo-shi, Ehime (JP)

(72) Inventor: Satoru Sakaguchi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 195 days.

(21) Appl. No.: 14/389,307

(22) PCT Filed: Mar. 28, 2013

(86) PCT No.: PCT/JP2013/059263
§ 371 (c)(1),
(2) Date: Sep. 29, 2014

(87) PCT Pub. No.: WO2013/147025
PCT Pub. Date: Oct. 3, 2013

(65) Prior Publication Data
US 2015/0057633 A1    Feb. 26, 2015

(30) Foreign Application Priority Data
Mar. 30, 2012   (JP) ................. 2012-082890

(51) Int. Cl.
*A61F 13/15* (2006.01)
*A61F 13/533* (2006.01)
*A61F 13/49* (2006.01)
*A61F 13/532* (2006.01)
*A61F 13/494* (2006.01)
*A61F 13/531* (2006.01)
*A61F 13/47* (2006.01)

(52) U.S. Cl.
CPC ...... *A61F 13/533* (2013.01); *A61F 13/15203* (2013.01); *A61F 13/49017* (2013.01);
(Continued)

(58) Field of Classification Search
CPC .......... A61F 13/533; A61F 2013/15357; A61F 2013/5312; A61F 13/5323; A61F 13/4704; A61F 13/4702
(Continued)

(56) References Cited

U.S. PATENT DOCUMENTS 6,702,800 B1   3/2004   Vukos et al.
7,993,321 B2   8/2011   Tani
(Continued)

FOREIGN PATENT DOCUMENTS

JP      2004-057413 A    2/2004
JP      2004-174210 A    6/2004
(Continued)

OTHER PUBLICATIONS

Extended European Search Report dated Oct. 6, 2015, corresponding to European Patent Application No. 13770260.1.
(Continued)

*Primary Examiner* — Jacqueline Stephens
(74) *Attorney, Agent, or Firm* — Hauptman Ham, LLP (57) ABSTRACT

An absorber of a disposable diaper includes a first region arranged partially in the crotch region; a second region arranged adjacent to the first region and having a lower bending rigidity than that of the first region; and a third region arranged adjacent to the second region and having a higher bending rigidity than that of the second region. A boundary between the first and second regions is arranged in a narrow region. A boundary between the second and third regions is arranged at the side of the crotch region from an end at the crotch region side of a waistline retaining unit in the front waistline region. An end at the front waistline region side of the third region is arranged at the side of the front waistline region from the end at the crotch region side of the waistline retaining unit in the front waistline region.

10 Claims, 5 Drawing Sheets (52) U.S. Cl.
CPC .... *A61F 13/49406* (2013.01); *A61F 13/5323* (2013.01); *A61F 13/4702* (2013.01); *A61F 13/4704* (2013.01); *A61F 2013/15357* (2013.01); *A61F 2013/5312* (2013.01)

(58) Field of Classification Search
USPC ................................ 604/378, 380, 381, 379
See application file for complete search history.

(56) References Cited

U.S. PATENT DOCUMENTS

| | | | |
|---|---|---|---|
| 2003/0119401 A1 | 6/2003 | Chakravarty et al. | |
| 2006/0058761 A1* | 3/2006 | Kudo | A61F 13/535 604/380 |
| 2010/0069874 A1* | 3/2010 | Noda | A61F 13/4758 604/385.23 |
| 2013/0110075 A1 | 5/2013 | Mukai et al. | |

FOREIGN PATENT DOCUMENTS

| | | |
|---|---|---|
| JP | 2008-253289 A | 10/2008 |
| WO | 03/026545 A2 | 4/2003 |
| WO | 2011/132688 A1 | 10/2011 |

OTHER PUBLICATIONS

Office Action dated Jun. 18, 2015, corresponding to Chinese patent application No. 201380016636.9.
International Search Report mailed Apr. 23, 2013 in International Application No. PCT/JP2013/059263 filed Mar. 28, 2013.
Office Action in AU Application No. 2013241168, mailed Nov. 4, 2016.

* cited by examiner

DISPOSABLE DIAPER

RELATED APPLICATIONS

The present application is a National Phase of International Application Number PCT/JP2013/059263, filed Mar. 28, 2013, which claims priority to Japanese Application Number 2012-082890 filed Mar. 30, 2012.

TECHNICAL FIELD

The present invention relates to a disposable diaper.

BACKGROUND ART

Conventionally, as for an open-type disposable diaper which has a front waistline region, a rear waistline region, a crotch region, a pair of leg hole openings, and an absorber spanning the crotch region and extending to the front waistline region and rear waistline region, a disposable diaper configured that a length in the product widthwise direction of the absorber is smaller in the crotch region as compared to the rear waistline region and the front waistline region (for example, see Patent Literature 1).

According to the disposable diaper having the absorber described above, a width of the absorber arranged in the crotch region having the narrowest interval between the legs of a wearer is small enough to arrange the absorber without interfering with a movement of the legs.

CITATION LIST

Patent Literature

[PTL 1]
Japanese Unexamined Patent Application Publication No. 2004-174210

SUMMARY OF INVENTION

However, the aforementioned disposable diaper has the below-mentioned problem.

As described above, the crotch region of the absorber is a part positioned between the both legs of a wearer as well as a part to which the force in a direction from the outer side to the inner side in the widthwise direction is applied by the legs or the like of a wearer. A length in the product widthwise direction of the absorber in the crotch region is smaller as compared to the front waistline region and the rear waistline region, and becomes even smaller in a case of application of the external force towards the inner side in the widthwise direction. Especially in the front waistline region and the crotch region adjacent to the front waistline region, in a case when they are sandwiched between the both legs, the force in a direction from the outer side to inner side in the widthwise direction is applied to the absorber in association with the inguinal portion as well, and a length in the widthwise direction becomes even smaller. As described above, in a case where a length in the widthwise direction of the absorber becomes small, the absorber is not arranged along the body to result in reduction in the fitting property, thereby leading to a possibility of the leakage of bodily fluid.

Furthermore, in a case where a crotch portion of the absorber is pressed towards the inner side in the widthwise direction, folding wrinkles extending in the longitudinal direction are formed in the absorber, and these folding wrinkles are propagated into the front waistline region side, thereby leading to a possibility that a length in the product widthwise direction becomes small in the entire absorber. In a case where a length in the product widthwise direction of the absorber becomes small, the absorber cannot be arranged along the body, thereby leading to a possibility of the leakage of bodily fluid.

Therefore, the present invention has been achieved in view of the above-described situation, and an object thereof is to provide a disposable diaper configured that a length in the product widthwise direction of the absorber is made smaller in the crotch region as compared to the front waistline region, the disposable diaper which prevents the absorber arranged at the abdominal side from deforming in the widthwise direction to thereby prevent the leakage of bodily fluid or reduction of the fitting property.

Solution to Problem

The disposable diaper (disposable diaper 10) according to the present disclosure is summarized as a disposable diaper including; a front waistline region (front waistline region 20); a rear waistline region (rear waistline region 30); a crotch region (crotch region 25) positioned between the front waistline region and the rear waistline region; a product longitudinal direction (product longitudinal direction L) from the front waistline region towards the rear waistline region; a product widthwise direction (product widthwise direction W) perpendicular to the product longitudinal direction; and an absorber (absorber 40) running across the crotch region and extending to the front waistline region and rear waistline region; and a waistline retaining unit (waistline retaining unit 80) that retains the disposable diaper around a body of a wearer, in the front waistline region and the rear waistline region; wherein the absorber is provided with a narrow region (narrow region 46) that a length in the widthwise direction of the absorber becomes smaller towards an inner side in the product longitudinal direction; a length of the absorber in the crotch region in the product widthwise direction is smaller than a length of the absorber in the front waistline region and a length of the absorber the rear waistline region in the product widthwise direction; the absorber includes: a first region arranged at least partially in the crotch region; a second region arranged adjacent to the first region at an outer side from the first region in the product longitudinal direction and having a lower bending rigidity than that of the first region; and a third region arranged adjacent to the second region at an outer side from the second region in the product longitudinal direction and having a higher bending rigidity than that of the second region; a boundary between the first region and the second region is arranged at the side of the front waistline region from a center of the disposable diaper in the product longitudinal direction and is arranged in the narrow region; a boundary between the second region and the third region is arranged at the side of the crotch region from an end at the crotch region side of the waistline retaining unit in the front waistline region; and an end at the front waistline region side of the third region is arranged at the side of the front waistline region from the end at the crotch region side of the waistline retaining unit in the front waistline region.

DESCRIPTION OF EMBODIMENTS

Hereinafter, an embodiment of a disposable diaper according to the present invention is described with reference to accompanying drawings. In the following description of the drawings, the same or similar reference numerals are used to designate the same or similar units. It will be appreciated that the drawings are schematically shown and the ratio and the like of each dimension are different from the real ones.

Accordingly, specific dimensions should be determined in consideration of the explanation below. Moreover, among the drawings, the respective dimensional relations or ratios may differ.

(1) Overall Schematic Configuration of Disposable Diaper

Figure 1:
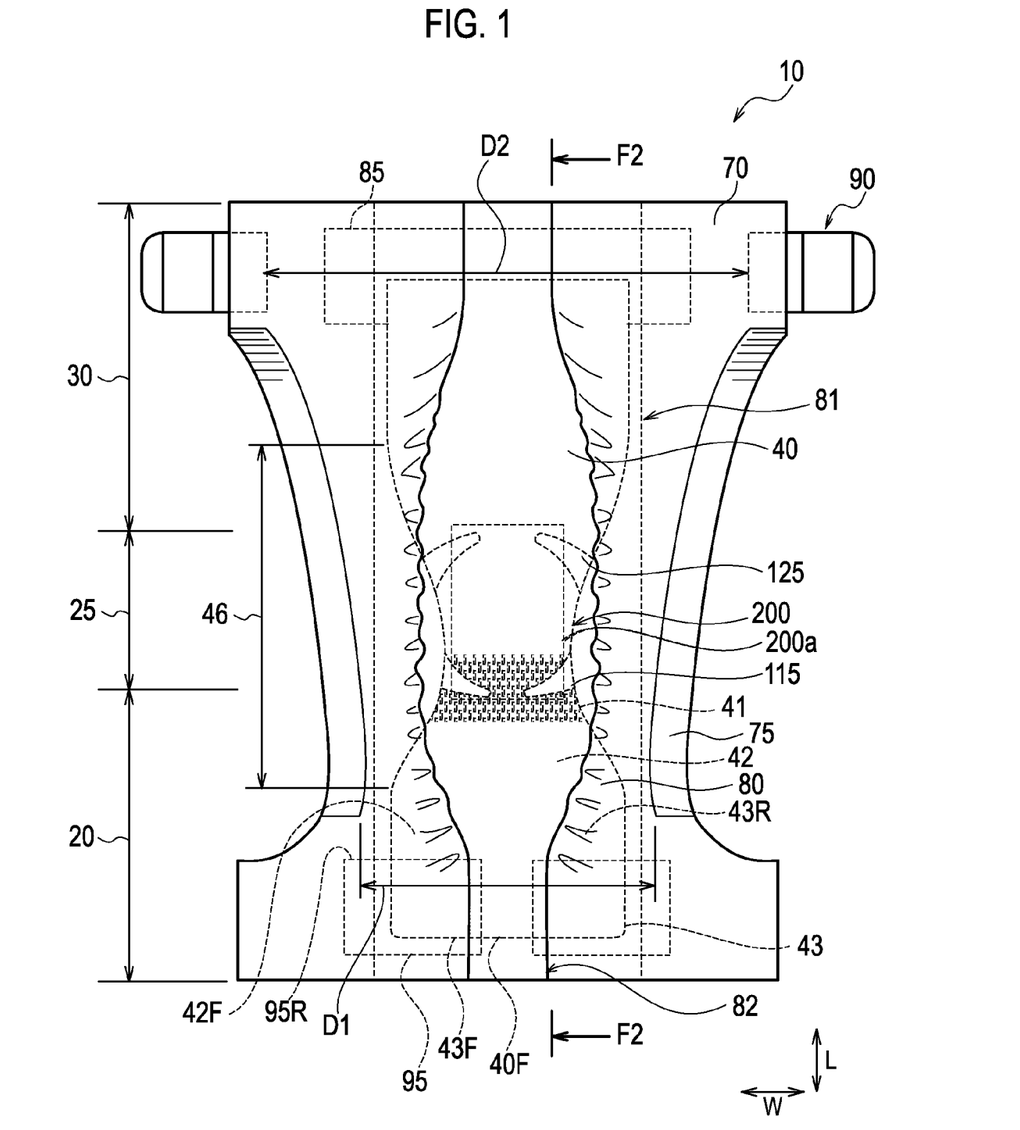
FIG. 1 is an exploded plan view of a disposable diaper according to a present embodiment.
Figure 2:
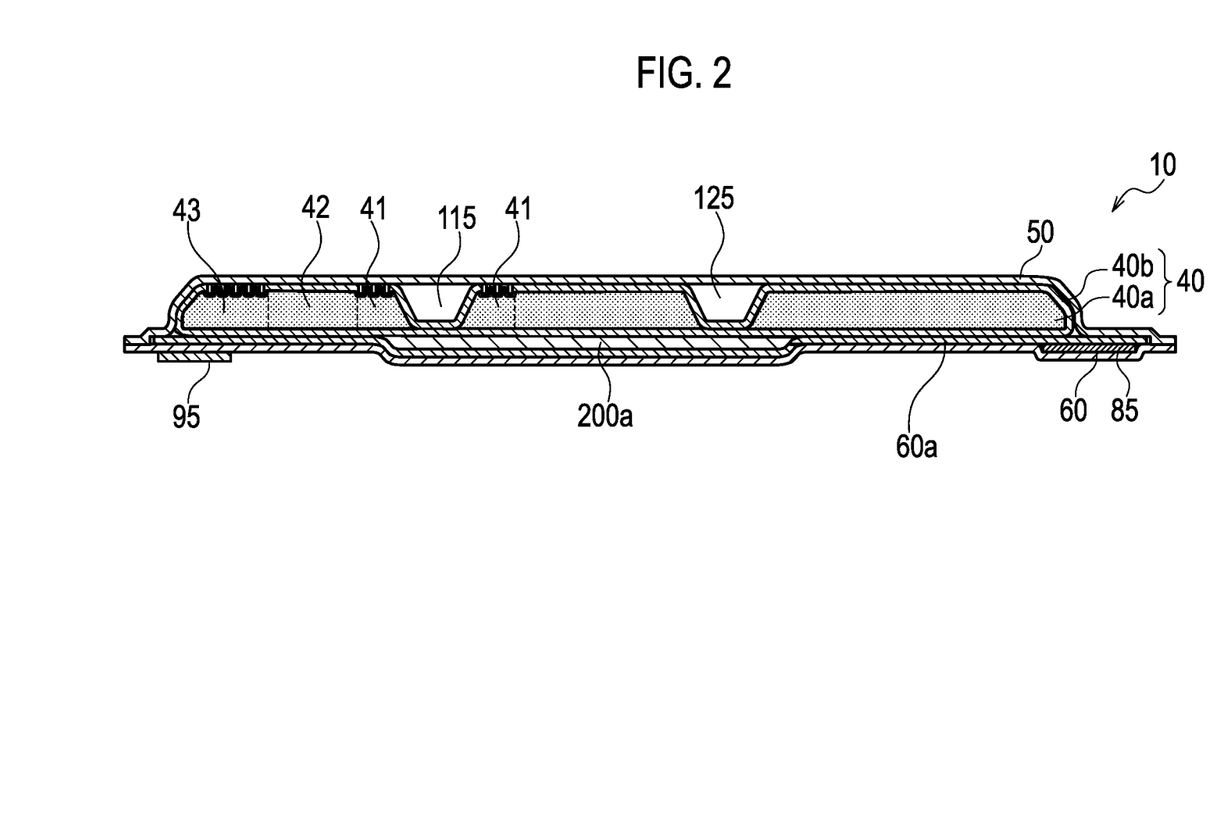
FIG. 2 is a cross-sectional view of the disposable diaper taken along the line F2-F2 shown in FIG. 1.

FIG. 1 is an exploded plan view of a disposable diaper 10 according to the present embodiment. FIG. 2 is a cross-sectional view of the disposable diaper 10 taken along the line F2-F2 shown in FIG. 1. It should be noted that the exploded plan view of FIG. 1 is a diagram in which leg stretch units 75 and leg side gathers 80 are in an expanded state such that wrinkles are not formed in a topsheet 50 and side flaps 70, for example, that configure the disposable diaper 10, but for the sake of description, the leg side gathers 80 are illustrated in a contracted state.

The disposable diaper 10 has a front waistline region 20, a crotch region 25, and a rear waistline region 30. The front waistline region 20 is a part coming in contact with the front waistline portion (abdominal portion) of a wearer. Furthermore, the rear waistline region 30 is a part coming in contact with a rear waistline portion (dorsal portion) of a wearer. The crotch region 25 is positioned between the front waistline region 20 and the rear waistline region 30. Furthermore, the disposable diaper 10 is provided with a pair of leg hole opening 35 (see FIG. 5). The leg hole openings 35 are provided at side edges in the widthwise direction of the disposable diaper and are parts which are arranged along the leg holes of a wearer in a state in which the disposable diaper is worn by a wearer.

In the present embodiment, the direction from the front waistline region 20 towards the rear waistline region 30 is called the product longitudinal direction L, and the direction perpendicular to the product longitudinal direction L is called the product widthwise direction W.

The disposable diaper 10 includes an absorber 40 spanning the crotch region 25 and extending to the front waistline region 20 and the rear waistline region 30. The absorber 40 is made up of an absorbent core 40a and a core wrap 40b.

The absorbent core 40a is same as in the conventional disposable diaper, and can be configured appropriately by using popular components and materials, such as ground pulp and high absorbent polymer. The absorbent core 40a is wrapped in the sheet-like core wrap 40b. The core wrap 40b is a sheet for wrapping at least a part of the absorbent core 40a. A part of at least the skin surface contact side of the core wrap 40b is made from various fibrous nonwoven fabrics or a tissue sheet having liquid-permeability. For example, an air-through fibrous nonwoven fabric, a spunbond nonwoven fabric, or an SMS (spunbond-meltblown-spunbond) nonwoven cloth having a mass of approximately 10 to 30 g/m2, or a tissue sheet having a mass of approximately 10 to 30 g/m2 can be used.

A liquid-permeable topsheet 50 is provided at the top side (skin contact surface side) of the absorber 40. Furthermore, a liquid-impermeable backsheet 60a is provided at the back side (non-skin contact surface side) of the absorber 40.

Side flaps 70 are provided at side edges in the product widthwise direction W of the absorber 40, respectively. The side flap 70 is made of one or two or more pieces of nonwoven fabrics overlapping one another. Furthermore, the pair of side flaps 70 are provided with the fastening tapes 90, respectively.

The fastening tapes 90 extend in the product widthwise direction W in the rear waistline region 30 and are fixed to target units 95 in the front waistline region to thereby retain the disposable diaper 10 to the body of a wearer.

The target units 95 are at least partially arranged in an absorber arrangement region in which the absorber is arranged, and are configured so that the pair of fastening tapes 90 are fixed to the target units 95, respectively. In the present embodiment, the front waistline 20, the rear waistline 30, the target units 95, and the fastening tapes 90 make up a front waistline retaining unit.

Furthermore, the disposable diaper 10 is formed in the crotch region 25 and includes a crotch stretch unit 200a which can expand and contract in the product longitudinal direction L. Specifically, the crotch stretch unit 200a is arranged in a crotch unit 200 formed in the crotch region 25. Configurations of the crotch unit 200 and the crotch stretch unit 200a are described later in details.

The top side (topsheet 50 side) of the absorber 40 is formed in the vicinity of the leg hole openings 35, and a pair of leg stretch units 75 which can expand and contract in the product longitudinal direction L are provided.

The leg stretch units 75 are longer in the product longitudinal direction L than the crotch stretch unit 200a while being provided at the outer side in the product widthwise direction W of the crotch stretch unit 200a. As long as the leg stretch units 75 are configured to make the leg hole opening 35 stretchable in the product longitudinal direction, the leg stretch units 75 may be arranged along the leg hole openings 35 or may be arranged with part of the leg stretch units 75 being inclined with respect to the leg hole openings 35.

Furthermore, the leg stretch units 75 are parts which are substantially contracted in the product longitudinal direction by means of a stretchable sheet or the like, and are a concept that excludes the part to which the stretchable sheet is arranged in a state in which no contraction force is exerted.

The leg stretch units 75 according to the present embodiment are made of stretchable members. For example, a stretchable film formed by melting a thermoplastic elastomer resin, such as urethane and styrene, and then converting into the shape of a film; a stretchable nonwoven fabric made from stretchable fibers; a composite sheet obtained by pasting an inextensible sheet partially cut or made fragile, to the stretchable film or the stretchable nonwoven fabric; or the like can be used as the aforementioned stretchable sheet.

Furthermore, in place of the stretchable sheet, the leg stretch units 75 may also be formed by arranging one or more thread-like or stripe-like elastic members made from polyurethane elastic fibers or natural rubber.

At least in the crotch region 25, a width (a width in the product widthwise direction W in of the disposable diaper 10 in a natural state) of the stretchable sheets making up the leg stretch units 75 is preferably 5 mm to 45 mm, more preferably 12.5 mm to 35 mm. In a case of a width smaller than 5 mm, the leg stretch units 75 follow the leg holes of a wearer by substantially using their surfaces, so that the fastening force does not concentrate partially, so that the elastic members cannot exhibit the effect of reducing the load on the skin. In a case of a width greater than 45 mm, a region following the leg holes widens too much in comparison to a length in the product widthwise direction of the entire disposable diaper, so that the stretchable sheets are easily caught on the body side of a wearer or turned up.

The ratio of expansion and contraction of the leg stretch units 75 is preferably 1.6 times to 2.4 times. In the present embodiment, the ratio of expansion and contraction of the leg stretch units 75 is set to 2.0 times. It is to be noted that a ratio of expansion and contraction means degree of expansion and contraction of the leg stretching unit 75 in an expansion and contraction direction (the product longitudinal direction L in the present embodiment) and is determined as follows.

The ratio of expansion and contraction of the leg gathers 75=(Length of the leg gathers 75 during maximum extension)/(Length of the leg gathers 75 in the natural state)

If the disposable diaper 10 is inserted in a package, take the diaper out of the package, and use a sample that has been kept in such a condition for 12 hours in an ambient temperature of 20° C.±2° C., and a relative humidity of 60%±5% RH.

Next, use a spring measure (tape: covered with glass fiber reinforced vinyl chloride) manufactured by Shinwa Rules Co., Ltd., keep it along the area to be measured, and measure the length of the disposable diaper 10 in this state, that is, the length of the leg gathers 75 when the disposable diaper 10 is in the natural state, and the length of the leg gathers 75 when the disposable diaper 10 is extended from its natural state until wrinkles caused by the elastic members are not visible to the naked eye. The above measurement was performed for 10 samples, and the average value was assumed as the aforementioned length.

Hereinafter, the measurement of the "length" described in the specification will be performed based on the aforementioned measuring method.

Furthermore, the interval between the inner ends of the pair of right-left leg stretch units 75 in the product widthwise direction W widens from the crotch region 25 towards the front waistline region 20, and also widens from the crotch region 25 towards the rear waistline region 30. By arranging the leg stretch units in a shape that is narrowed in the crotch portion and widened towards the front and rear waistlines, the leg stretch units can follow a line of the body, thereby being able be suitably arranged in an extended state around the leg holes of a wearer.

Further, the interval (D1 in the drawings) between the pair of right-left leg stretch units 75 at the end of the front waistline region 20 is smaller than the interval (D2 in the drawings) between the pair of right-left leg stretch units 75 at the end of the rear waistline region 30. It should be noted that these intervals are obtained by measuring a distance between the inner ends in the product widthwise direction W of the pair of right-left leg stretch units 75 after the disposable diaper 10 is shifted from the natural state to a state free from wrinkles by stretching out and retaining the disposable diaper 10 in the product longitudinal direction L and the product widthwise direction W.

A stretch of the skin surface of the body of a wearer is large especially in the hip portion and stands out in a position closer to the outer side in the widthwise direction of the hip portion. Furthermore, the leg stretch units 75 are in close contact with the body of a wearer. Thus, with a configuration of D2>D1, even in a case where the disposable diaper 10 is given a movement of a wearer, the leg stretch units 75 at the hip portion side can be stretched out while keeping tight contact, so that the leg stretch units 75 are not projected even if the stretch has the large amount of change. Accordingly, it is possible to prevent shifting of the disposable diaper 10 due to the leg stretch units 75.

Further, a pair of leg side gathers 80 extending in the product longitudinal direction L are provided in the inner side (closer to the center in the product widthwise direction W) of the pair of leg stretch units 75. The leg side gathers 80 are provided at the inner ends in the product widthwise direction of the side flaps, and are orthostatic stretch gathers arranged at the inner side in the product widthwise direction of the leg stretch units. Each of the side flaps is folded over towards the topsheet side at the inner end in the product widthwise direction to form a lamination of two layers. An elastic member 76 (see FIG. 2) is provided in an extended state in the longitudinal direction, between the two layers of the side flap. This side flap 70 and the elastic member 76 form the leg side gather 80.

Each of the leg side gathers 80 has a joining part 81 to be joined to a backsheet 60a, and a free end portion 82 positioned at the opposite side of the joining part 81 and provided with an elastic member (not shown in FIG. 1). As for the leg side gather 80, when the diaper is worn, the joining part 81 rises up as the proximal end and the free end portion 82 comes in contact with the skin of a wearer as the apex.

It should be noted that the backsheet 60a is arranged between the absorber 40 and an exterior sheet 60 and functions as a leakage-preventing sheet.

Furthermore, the joining part 81 of the leg side gathers 80 may be joined to the exterior sheet 60.

Furthermore, the end in the product longitudinal direction L of the free end portion 82 of the leg side gather 80 is joined to the topsheet 50. The joining part 81 is arranged between the crotch stretch unit 200a and the leg stretch unit 75 in the product widthwise direction W.

The joining part 81 of the leg side gather 80 can adopt various configurations. For example, the joining part may be a part extending in the product longitudinal direction from the crotch unit to the front waistline region and the rear waistline region and joined to the topsheet, or may be a part joined to the liquid-impermeable backsheet or the exterior sheet at the outer side in the widthwise direction of the absorbent core 40a, and is configured as the proximal end of rising.

Furthermore, as long as the leg side gather is an orthostatic gather arranged at the inner side in the product widthwise direction of the leg stretch unit, its configuration is not limited to the above, and it goes without saying that the conventionally known configuration of the leg side gather can be adopted.

Furthermore, a hipline stretch unit 85 which can expand and contract in the product widthwise direction is provided between the pair of fastening tapes in the product widthwise direction. A structural member of hipline stretch unit 85 is not particularly limited, but preferably used is a member having a thickness as small as possible, a low bending rigidity, and a small width reduction rate, such as a stretch film.

The hipline stretch unit 85 is stretched out 1.5 times to 2.5 times of a length in the unextended state (natural state) and thereafter bonded to the exterior sheet 60 by means of hot-melt adhesive, a heat treatment, or the like.

Figure 3:
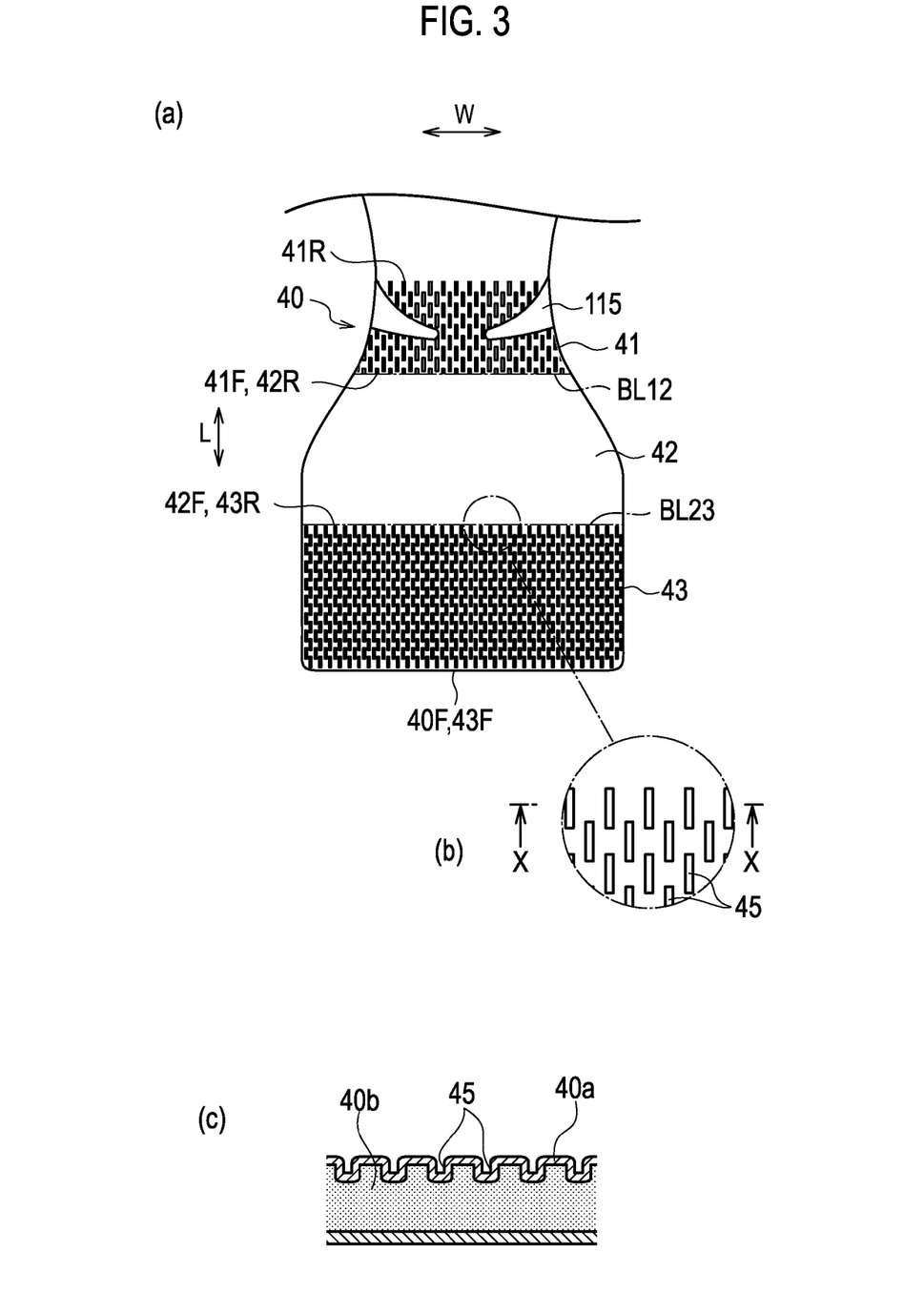
FIGS. 3a-c are diagrams illustrating an absorber according to the present embodiment.

In the present embodiment, the hipline stretch unit 85 is arranged between the exterior sheet 60 and the backsheet 60a (see FIG. 3). However, in a configuration that the core wrap 40b is projected towards the outer side in the product longitudinal direction of the absorbent core 40a, the hipline stretch unit 85 may be arranged between the core wrap 40b and the backsheet 60a or the exterior sheet 60. A position of the hipline stretch unit is not particularly limited but preferably arranged closer to the non-skin contact surface side than the absorber 40. Furthermore, in a region in which the absorber is not arranged, the hipline stretch unit 85 may be arranged between the side flaps 70 and the backsheet 60a or the exterior sheet 60.

In the plan view, the hipline stretch unit 85 is arranged between the pair of fastening tapes. The hipline stretch unit 85 contracts an interval between the fastening tapes in the widthwise direction.

It should be noted that the hipline stretch unit according to the present embodiment is configured so as to stretch in the product widthwise direction but may be configured so as to stretch in the product widthwise direction and the product longitudinal direction.

(2) Shape of Crotch Unit

Next, the shape of the crotch unit 200 is explained. As described above, the crotch unit 200 has the crotch stretch unit 200a. The crotch stretch unit 200 is configured so as to make it easy for the absorber 40 to keep its shape which is more flat than the other parts when the disposable diaper is worn. The crotch unit 200 includes the crotch stretch unit 200a which can expand and contract at least in the product longitudinal direction L or the product widthwise direction W.

The crotch stretch portion 200a is provided individually and independently of the leg stretch units 75, and is configured, in a position overlapped with the absorbent core 40a (in the present embodiment, a position between the core wrap 40a wrapping the absorbent core 40a and the backsheet 60a), so as to cause contraction by 60% or more of a length in the widthwise direction of the absorbent core 40a in the aforementioned overlapping position. As described above, by contracting the portion provided with the absorbent core 40a by means of the crotch stretch unit 200a, the absorbent core 40a is contracted, thereby easily keeping the flat shape as compared to the part in which the absorbent core 40a is not contracted.

On the other hand, the absorbent core 40a positioned in the front waistline region or the rear waistline region positioned at the outer side in the product longitudinal direction of the crotch stretch unit 200a is not contracted by means of the crotch stretch unit 200a, so that the crotch unit 200 is arranged along the body to a moderate degree without bringing the entire absorber in too tight contact with the body.

Furthermore, the crotch unit 200 is stretchable in the product longitudinal direction L, which makes it easy for the front waistline region 20 and the rear waistline region 30 to rise up in association with contraction of the crotch unit 200, thereby forming the flat crotch region along the body at the crotch of a wearer when the diaper is worn. The front waistline region and the rear waistline region rise up from the crotch stretch unit 200a, thereby improving the fitting property of the disposable diaper 10 into a wearer. The crotch stretch unit 200a is preferably made from the stretchable sheet. By making the crotch stretch unit 200a from the stretchable sheet, the absorbent core 40a in the region provided with the stretchable sheet is uniformly contracted, thereby making it easy to keep the flat shape. The stretchable sheet can be made from the same as that of the leg stretch unit 75, for example.

Furthermore, in place of the stretchable sheet, the crotch stretch portion 200a may also be configured by arranging one or more thread-like or stripe-like stretchable elastic members made from polyurethane elastic fibers or natural rubber. In such a case, in order to uniformly contract the absorbent core 40a by means of the crotch stretch unit 200a, an interval between the elastic members is set to preferably 7 mm or less, more preferably 5 mm or less. For the purpose of uniform contraction of the absorbent core 40a, a difference in the interval between adjacent elastic members is desirably 0.5 mm or less.

Furthermore, the ratio of expansion and contraction of the crotch stretch unit 200a is preferably 1.2 times or more and 1.8 times or less, specifically. In the present embodiment, the ratio of expansion and contraction of the crotch stretch unit 200a is set to 1.4 times.

The ratio of expansion and contraction of the crotch stretch unit 200a implies the extent of the expansion and contraction of the crotch stretch unit 200a in the direction of expansion and contraction (product longitudinal direction L), and is stipulated as below:

The ratio of expansion and contraction of crotch stretch unit 200a=(Length of the crotch unit during maximum extension)/(Length of the crotch unit in the natural state). It should be noted that the ratio of expansion and contraction as used herein is to be measured as described below, for example.

Firstly, in a case where the disposable diaper 10 is inserted in a package, for example, then the disposable diaper 10 is taken out of the package, and the diaper is kept in such a condition for 60 minutes in an ambient atmosphere having a temperature of 20° C.±2° C., and a relative humidity of 60%±5% RH, and then a length of the crotch stretch unit is measured i in the direction of expansion and contraction. This length is set to a "length i in the direction of expansion and contraction of the crotch stretch unit 200a in the natural state".

Secondly, measurement is performed with respect to the length in the direction of expansion and contraction of the desired region in this state (that is, in the natural state), and the length in the direction of expansion and contraction of the desired region when the disposable diaper is extended from its natural state to a state in which wrinkles caused by the elastic members cannot be visually confirmed. This length is set to a "length in the direction of expansion and contraction of the crotch stretch unit 200a in the maximum extended state".

As described above, by setting the ratio of expansion and contraction of the crotch stretch unit 200a to 1.2 times to 1.8 times, it is possible to favorably follow the stretching of the skin of the wearer.

For example, when the wearer is slouchy such that the front side of the body is cringing, in the skin at the side of the hip portion of the wearer, there is a region that stretches by approximately 30% as compared to the state when the body has been stretched out.

That is, when the ratio of expansion and contraction of the crotch stretch unit 200a is 1.2 times or less, the contraction of the crotch stretch unit 200a in the natural state is insufficient, and as compared to the case where the crotch stretch unit 200a has not been provided, the difference in the ease of curving of the disposable diaper 10 is small because of which the front waistline region 20 does not rise at the desired position.

On the other hand, when the ratio of expansion and contraction of the crotch stretch unit 200a is more than 1.8 times, the contraction size in the contraction direction of the crotch stretch unit 200a becomes too large, because of which the region where the crotch stretch unit 200a exists easily comes in close contact with the body of the wearer rather than running along it, and the disposable diaper 10 easily shifts to the lower side of the wearer.

Furthermore, the center in the product longitudinal direction L of the crotch stretch unit 200a is arranged closer to the front waistline region 20 side as compared to the center in the product longitudinal direction L of the disposable diaper 10. However, the crotch stretch unit 200a is arranged so as to span the center in the product longitudinal direction L of the disposable diaper 10.

In such a case, in view of the rigidity of the absorbent core 40a and the rigidity of other members configuring the disposable diaper 10, the thickness of the elastic members and the arrangement pitch can be selected appropriately. However, when the main body of the disposable diaper 10 is in the natural state (unextended state), the entire side edge in the product widthwise direction W of the absorbent core 40a is preferably in a contracted state.

Furthermore, the crotch region 25 of the absorber 40 is provided with a notch 115 (notch 125). The notches 115, 125 are regions without having the absorbent core 40a making up the absorber 40. In the present embodiment, the notches 115, 125 correspond to a low rigidity unit having a smaller basis weight of the absorbent core 40a than the other parts of the absorbent core 40a. It should be noted that instead of formation of the notches 115, 125, the regions of the notches 115, 125 may be configured to have a smaller basis weight of the absorbent core 40a than the other parts of the absorbent core 40a.

The notches 115, 125 exist along the edges in the product longitudinal direction L of the crotch unit 200. Even with the formation of the notches 115, 125, the absorbent core 40a positioned in the front waistline region 20 and the rear waistline region 30 is preferably continuous to the absorbent core 40a positioned in the crotch region 25 without complete separation, especially in the widthwise direction.

The length in the product longitudinal direction L of the notches 115, 125 widens towards the outer side in the product widthwise direction W. With such a shape, the outer side in the widthwise direction W of the absorbent core 40a is contracted more easily, thereby making it easier to form the flat "bottom". Furthermore, the absorbent core 40a positioned closer to the front waistline region 20 than the notch 115 and the absorbent core 40a positioned closer to the rear waistline region 30 than the notch 125 rise up from the "bottom" and are prone to be curved along the roundness of the body (abdominal portion and hip portion) of a wearer, so that the disposable diaper itself can be shaped more like the shape of the body of a wearer.

Furthermore, the edge closer to the front waistline region 20 (rear waistline region 30) of the notch 115 (notch 125) is arc-shaped. The edge of the notch 115 (notch 125) is shaped so that the center of the arc is positioned closer to the rear waistline region 30 (front waistline region 20) as compared to the edge itself. Such a shape realizes the deformation along the roundness of the body of a wearer more easily and prominently.

(3) Shape of Crotch Unit

Next, the shape of the absorber 40 is explained. FIG. 3 is a diagram illustrating the absorber 40. FIG. 3(a) is an enlarged plan view as seen from the topsheet 50 side, FIG. 3(b) is a partially enlarged view of FIG. 3(a), and FIG. 3(c) is an X-X cross-sectional view of FIG. 3(b).

The absorber 40 includes a first region 41 at least partially arranged in the crotch stretch unit 200a, a second region 42 arranged adjacent to the first region 41, at the front waistline region side than the first region 41, and having a lower bending rigidity than that of the first region 41, and a third region 43 arranged adjacent to the second region 42, at the front waistline region side than the second region 42, and having a higher bending rigidity than that of the second region 42.

The first region 41 and the third region 43 are provided in the entire absorber in the product widthwise direction. The first region 41 and the third region 43 are provided with a compressed unit 41 in which the absorber 40 is compressed in the product thickness direction. A plurality of compressed units 45 are formed intermittently across the entire first region 41. On the other hand, the second region 42 and the third region 43 are not provided with any compressed unit 45. Therefore, the first region 41 and the third region 43 are configured to have a higher bending rigidity than those of the second region 42 and the third region 43.

The bending rigidity in the present embodiment is based on a rigidity value in accordance with the taber method (JISP8125), and it can be confirmed by the measurement based on the following method. First, from the disposable diaper in the expanded state, a sample (for example, the absorber) of an object part for measuring a bending rigidity is collected. The sample is prepared for the measuring object part, in a size having a sample length of 70 mm in the product widthwise direction or the product longitudinal direction and a length of 38 mm in the widthwise direction perpendicular to the sample length direction. In a case where the sample contains a stretch elastic member therein, the elastic member is removed beforehand. It should be noted that as a tester for measuring a rigidity value, a taber stiffness tester manufactured by Yasuda Seiki Seisakusho, Ltd., is used. Furthermore, the number of samples is ten, in which each of the samples is measured and an average value is set as a rigidity value.

The measurement procedure is shown by the following (a) to (e).

(a) Thickness (A) of the collected sample is measured.

(b) Subsequently, the sample is sandwiched to an extent that it comes in contact with the center of a zipper (lower side) of the tester.

(c) Adjustment is made so that a total of right-left gaps between a supporting roller and the sample is set to (A)×0.80 (mm)

(d) An auxiliary weight is appropriately selected so that the designed load scale falls within 15 to 85% of the maximum scale.

(e) The sample is rotated in right and left directions and is stopped at the point that 15 degrees marking line and the center mark of the pendulum correspond to each other, and the scale of the tester is read. A numerical value at the left side of the scale is set as (B) while a numerical value at the right side of the scale is set as (C).

A rigidity value is obtained by the following expression.

$$\text{Rigidity value (mN·m)} = ((B)+(C))/2) \times (\text{Auxiliary weight coefficient}) \times 9.81 \times 10{-2} \quad \text{Expression:}$$

In a case where a width of the test piece cannot collect in a size of 38 mm, a conversion to a bending moment with a width of 38 mm is performed.

As the rigidity value thus measure is larger, the bending rigidity is higher, while the rigidity value is smaller, the bending rigidity is lower.

The plurality of compressed units 45 are configured so that the length in the product longitudinal direction is larger than the length in the product widthwise direction, and they are arranged in a staggered form. As described above, the compressed units 45 are discontinuously arranged in the staggered form, so that a compressed part and a non-compressed part are mixed in the first region 41 and the third region 43. The non-compressed part has the lower bending rigidity than that of the compressed part, thereby being deformable flexibly, which makes it possible to improve the bending rigidity of the first region 41 and the third region 43 while arranging the first region 41 and the third region 43 along a line of a curvy body.

The compressed unit 45 may be formed while being compressed in the thickness direction from the outer side of the core wrap 40b in a state in which the absorbent core 40a is wrapped in the core wrap 40b, or may be formed by making formation so that the absorbent material of the first region 41 has a higher basis weight than that of the absorbent material of the second region 42 at the time of laminating the absorbent materials making up the absorbent core 40a, and by compressing the absorbent core 40a in the thickness direction.

Furthermore, the absorber according to the present embodiment is configured so that the bending rigidity of the first region 41 is made high by formation of the compressed units 45. However, other configuration may be adopted to configure the absorber so that the bending rigidity of the first region 41 is made higher than those of the second region 42 and the third region 43.

As long as a bending rigidity of the first region and a bending rigidity of the third region are set higher than that of the second region, a bending rigidity of the first region may be set higher or lower than that of the third region.

Furthermore, the absorbent core 40a of the absorber 40 is provided with a narrow region 46 in which a length in the product widthwise direction of the absorber becomes smaller towards the inner side in the product longitudinal direction. The absorbent core 40a of the absorber 40 is configured that a length in the product widthwise direction in the crotch region of the absorber is set smaller than lengths in the product widthwise direction of the front waistline region and the rear waistline region.

An end 41R at the rear waistline region side of the first region 41 extends in the widthwise direction by passing through the inner end in the product longitudinal direction of the notch 115, and is arranged closer to the rear waistline region side than the end at the front waistline region side of the crotch stretch unit. Accordingly, a part of the first region 41 is arranged by overlapping with the crotch stretch unit 200a.

An end 41F at the front waistline region side of the first region 41 is arranged closer to the front waistline region side than the center in the product longitudinal direction of the disposable diaper, and is arranged inside the narrow region 46. The end 41F at the front waistline region side of the first region 41 also functions as an end 42R at the rear waistline side of the second region 42, and is a boundary between the first region and the second region.

A boundary between the first region 41 and the second region 42 and a boundary between the second region 42 and the third region 43 are arranged along the product widthwise direction W. FIG. 3 shows a boundary line BL12 virtually showing the boundary between the first region 41 and the second region 42, and a boundary line BL13 virtually showing the boundary between the first region 41 and the third region 43.

The boundary between the second region and the third region is an end 42F at the front waistline region side of the second region as well as an end 43R at the rear waistline region side of the third region. The boundary between the second region and the third region is arranged closer to the crotch region side than the end of the crotch region side of the waistline retaining unit in the front waistline region. In the present embodiment, the waistline retaining unit in the front waistline region is a region extending in the widthwise direction from a region provided with the target unit 95. Therefore, the boundary between the second region and the third region is arranged closer to the crotch region side than an end 95R at the crotch region side of the target unit 95.

An end 43F at the front waistline region side of the third region is arranged closer to the front waistline region side than the end at the crotch region side of the waistline retaining unit in the front waistline region. In other words, the end 43F at the front waistline region side of the third region is arranged closer to the front waistline region side than the end 95R at the crotch region side of the target unit 95.

It should be noted the absorber 40 according to the present embodiment is configured that the end 43F at the front waistline region side of the third region 43 corresponds to the end 40F at the front waistline region side of the absorber 40, but it is preferable that the end 43F at the front waistline region side of the third region 43 do not correspond to the end 40F at the front waistline region side of the absorber 40. In a case of configuration that the end 40F of the front waistline region of the absorber 40 is given a high bending rigidity, the fitting property is improved to possibly give the feeling of discomfort around the hipline of a wearer. However, by arranging the end 43F at the front waistline region side of the third region 43 closer to the rear waistline region side than the end 40F at the front waistline region side of the absorber, the feeling of discomfort can be prevented around the hipline.

In a state in which a so-called disposable diaper is worn by a wearer, the disposable diaper is retained by the waistline retaining unit to the waistline of a wearer. Furthermore, the crotch region connects the front waistline region and the rear waistline region and comes in contact with the crotch of a wearer. When a wearer wearing the disposable diaper thus configured moves his or her legs, the force is applied to the absorber or the like in a state in which the waistline retaining unit and the crotch region are brought in close contact with the wearer. Specifically, the crotch region of the absorber receives application of the force exerted from the outer side to the inner side in the widthwise direction.

However, the crotch region at the abdominal side of the absorber is provided with the first region 41 having a relatively high bending rigidity, so that the first region 41 can prevent deformation of the crotch region 25 of the absorber 40. Therefore, a length in the widthwise direction of the absorber in the crotch region, which is relatively small in the natural state, can be prevented from becoming even smaller. Thus, it is possible to prevent reduction of the fitting property or the leakage of bodily fluid.

Furthermore, the second region having a relatively low bending rigidity is provided adjacent to the first region. The end 42F at the front waistline region side of the second region 42 is arranged inside the narrow region 46. This narrow region is a part in which a width of the absorber becomes small and the force towards the inner side in the widthwise direction is prone to be applied in association with the inguinal portion. Because of formation of the second region in this narrow region, even in a case where the force is applied in association with the inguinal portion, the absorber can be prevented from deforming and be easily arranged along the body.

As described above, the second region is provided adjacent to the first region, the first region 2 can deform to absorb the external force at the time of application of the force to the absorber, thereby being able to prevent deformation of the crotch region or the third region. Furthermore, for example, in a case where folding wrinkles are formed in the first region, the second region can absorb the folding wrinkles to prevent the folding wrinkles from propagating into the third region.

Furthermore, the third region is arranged by at least partially overlapping with the waistline retaining unit in the longitudinal direction. The third region can make it difficult for the waistline retaining unit for retaining the disposable diaper around a wearer to be bent, thereby being able to keep close contact of the waistline.

In the absorber, by increasing a bending rigidity of a part (waistline retaining unit) for retaining the disposable diaper and a part (crotch region) to which the external force is easily applied, and decreasing a bending rigidity of an interval between these parts, even in a case where the absorber is pressed towards the inner side in the widthwise direction by the legs and the inguinal portion, it is possible to prevent formation of folding wrinkles in the entire absorber arranged at the abdominal side. Therefore, the absorber arranged at the abdominal side can be arranged along the body in a smooth state, thereby being able to prevent the leakage of bodily fluid.

As described above, the crotch region 25 is pulled up towards a wearer's side by means of the crotch stretch unit 200a which is contracted at least in the product longitudinal direction. Therefore, the crotch unit 200 is arranged in a position close to a wearer. Accordingly, the absorber 40 can be easily arranged along the position close to the body even in a case where a weight or load is applied from outside.

Furthermore, the crotch stretch unit 200a is contracted at least in the product longitudinal direction, thereby having a higher bending rigidity as compared to the periphery which is not contracted. There are/is the leg stretch unit 75 and/or the leg side gathers 80 in the product longitudinal direction in excess of the ends of the front waistline region side and rear waistline region side of the crotch stretch unit 200a. Therefore, inflection points are provided at the both ends in the longitudinal direction of the crotch stretch unit 200a, thereby causing the deformation so that the crotch stretch unit is set as the bottom.

The crotch stretch unit 200a positioned in the crotch region 25 forms the bottom, and can be arranged so as to face to the crotch of a wearer. Furthermore, the parts closer to the front waistline region side and the rear waistline region side than the crotch stretch unit 200a are deformed so as to rise up towards a wearer's side based on the outer ends in the product longitudinal direction of the crotch stretch unit. The crotch stretch unit 200a is arranged by being partially overlapped with the first region, so that the deformation by the crotch stretch unit 200a can be propagated into the abdominal side, thereby making it easy to arrange the front waistline region along the body of a wearer.

Furthermore, the crotch stretch unit 200a is made by an elastic element such as a stretchable sheet or the like, so that even at the time of deformation upon the external force, it is restored to the natural state. Therefore, in a case where the force for narrowing a width of the crotch unit 200 is applied by a wearer, the crotch unit 200 is restored to its original state. By formation of the crotch stretch unit 200a, width reduction of the crotch region 25 can be prevented together with the first region 41.

Figure 4:
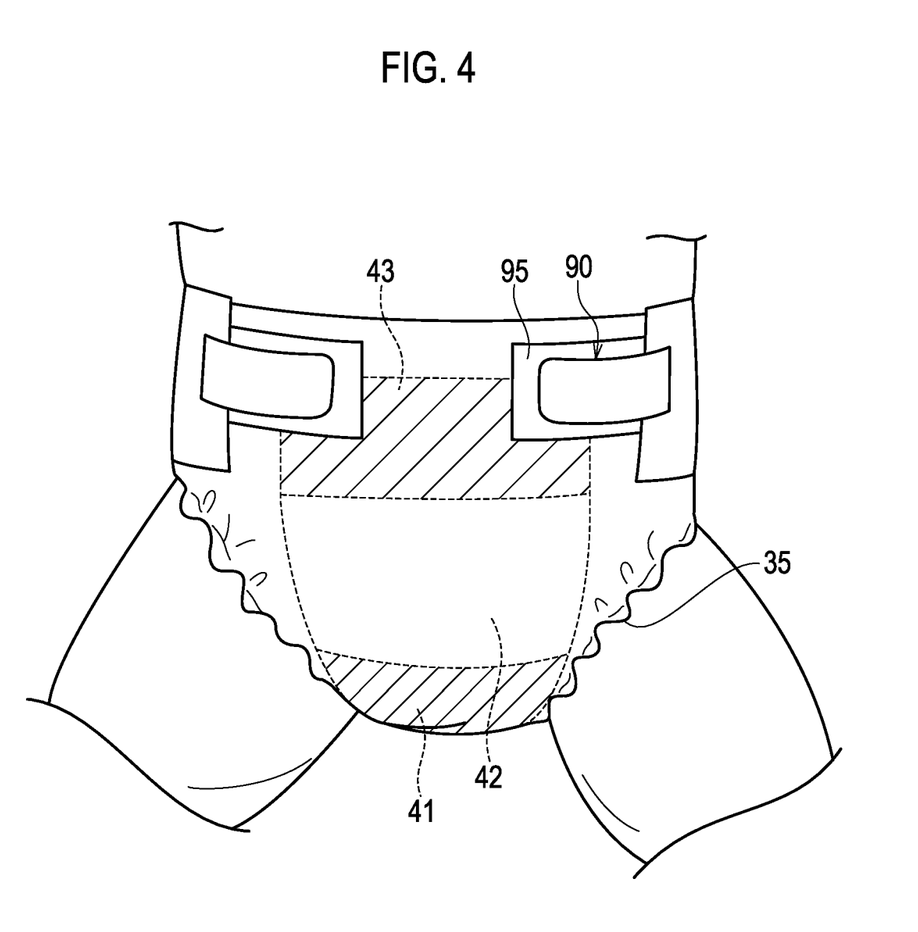
FIG. 4 is a diagram illustrating schematically a state in which the disposable diaper according to the present embodiment is worn by a wearer.
Figure 5:
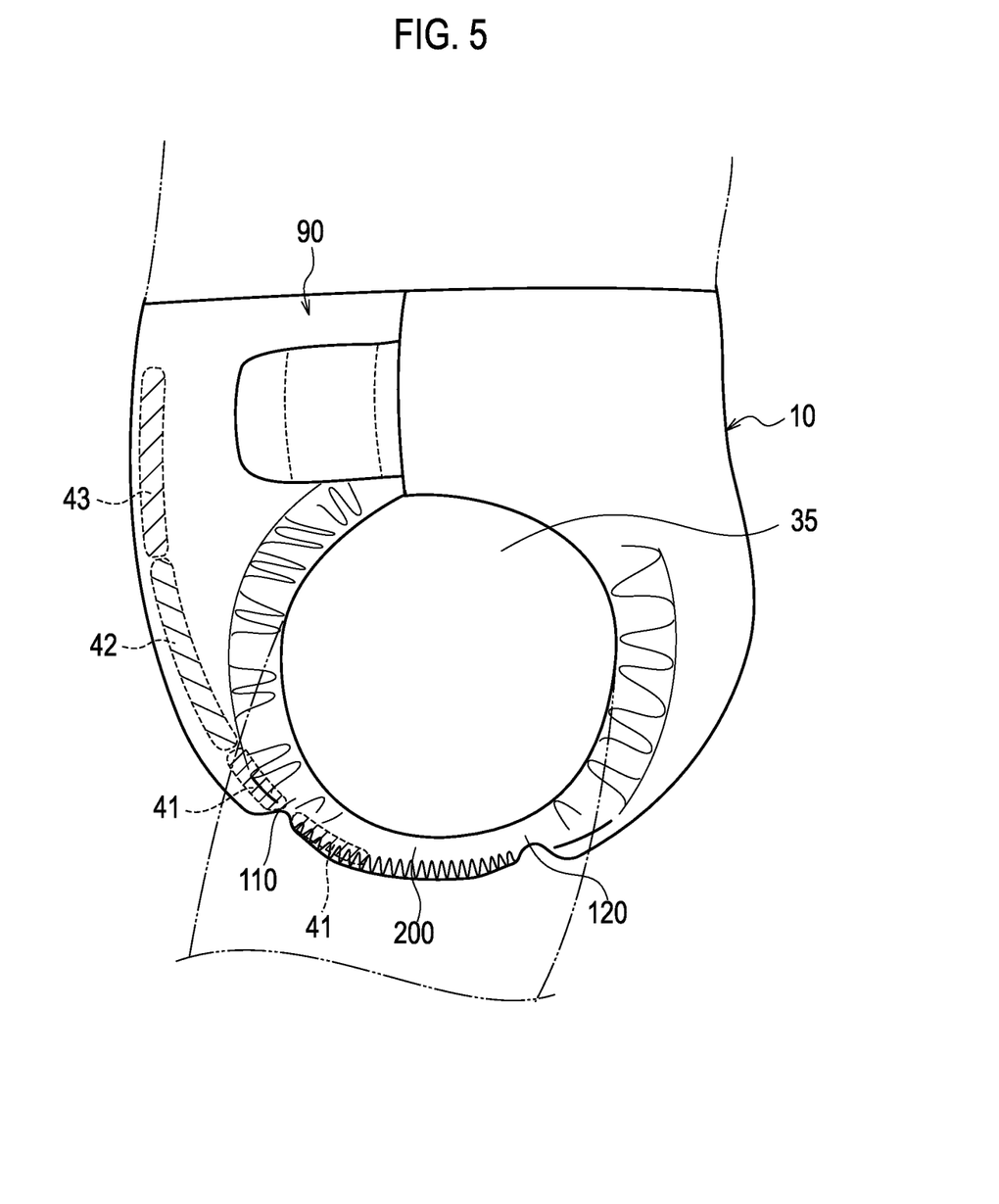
FIG. 5 is a diagram illustrating schematically a state in which the disposable diaper according to the present embodiment is worn by a wearer.

FIGS. 4 and 5 are diagrams each illustrating schematically a state in which the disposable diaper according to the present embodiment is worn by a wearer. For convenience of explanation, FIGS. 4 and 5 illustrate schematically the first region 41, the second region 42, and the third region 43 arranged insider the disposable diaper.

Since the region overlapped with a part of the waistline retaining unit of the disposable diaper is provided with the third region 43 having a relatively high bending rigidity, the third region makes it difficult for the waistline retaining unit for retaining the disposable diaper around a wearer to be bended, thereby being able to keep close contact of the waistline.

Furthermore, since the first region having a relatively high bending rigidity is arranged in the crotch region, even in a case of application of the force from the outer side to the inner side in the product widthwise direction, it is possible to prevent a length in the widthwise direction from becoming too small.

The narrow region 46 in the front waistline region is a region supposed to be inflected smoothly along the body's line so that the disposable diaper 10 extends from the abdominal side waistline toward the crotch portion of a wearer. Since the second region having a relatively low rigidity is provided inside the concave region 46, even in a case where the force in a direction from the outer side to the inner side in the widthwise direction is applied to the absorber by the inguinal portion as well, the second region is deformed and arranged along the body. Therefore, the first region and the third region can be arranged in a smooth state along the body, while the second region can be smoothly arranged along the inguinal portion.

(4) Operation and Effect

The first region 41 having a relatively high bending rigidity is provided in the crotch region at the abdominal side of the absorber, so that the first region 41 can prevent deformation of the crotch region 25 of the absorber 40. Therefore, a length in the widthwise direction of the absorber in the crotch region, which is relatively small in the natural state, can be prevented from becoming even smaller. Thus, it is possible to prevent reduction of the fitting property or the leakage of bodily fluid.

The second region having a relatively low bending rigidity is arranged adjacent to the first region. The end 42F at the front waistline region side of the second region 42 is arranged inside the concave region 46. This concave region is a part in which a width of the absorbent core of the absorber becomes small and the force towards the inner side in the widthwise direction is prone to be applied in association with the inguinal portion. Because of formation of the second region in this narrow region, even in a case where the force is applied in association with the inguinal portion, the absorber can be prevented from deforming and be easily arranged along the body.

The third region is arranged by at least partially overlapping with the waistline retaining unit in the longitudinal direction. The third region can make it difficult for the waistline retaining unit for retaining the disposable diaper around a wearer to be bent, thereby being able to keep close contact of the waistline.

In the absorber, by increasing a bending rigidity of a part (waistline retaining unit) for retaining the disposable diaper and a part (crotch region) to which the external force is easily applied, and decreasing a bending rigidity of an interval between these parts, even in a case where the absorber is pressed towards the inner side in the widthwise direction by the legs and the inguinal portion, it is possible to prevent formation of folding wrinkles in the entire absorber arranged at the abdominal side. Therefore, the absorber arranged at the abdominal side can be arranged along the body in a smooth state, thereby being able to prevent the leakage of bodily fluid.

Therefore, it is possible to provide a disposable diaper configured that a length in the product widthwise direction of the absorber is made smaller in the crotch region as compared to the front waistline region, the disposable diaper which prevents the absorber arranged at the abdominal side from deforming in the widthwise direction to thereby prevent the leakage of bodily fluid or reduction of the fitting property.

Furthermore, the plurality of compressed units of the disposable diaper 10 are formed intermittently across the entire region of the first region and the third region. Thus, a bending rigidity can be made substantially equally high in the entire of the first region and the third region. Furthermore, the plurality of compressed units are arranged intermittently in the first region and the third region, so that the compressed part and the non-compressed part are mixed in the first region and the third region. The non-compressed part has a lower bending rigidity than that of the compressed part, thereby being deformable flexibly, which makes it possible to improve the bending rigidity of the first region 41 and the third region 43 while arranging the first region 41 and the third region 43 along a line of a curvy body.

Furthermore, since the crotch stretch unit 200a is provided in the absorber, the end in the product longitudinal direction of the crotch stretch unit 200a functions as an inflection point, which enhances the deformation of the absorber. Furthermore, the low rigidity unit is formed at a more inner side in the product longitudinal direction than the crotch stretch unit, the absorbent core 40a positioned closer to the front waistline region 20 than the low rigidity unit and the absorbent core 40a positioned closer to the rear waistline region 30 than the low rigidity unit rise up from the "bottom" and are prone to be curved along the roundness of the body (abdominal portion and hip portion) of a wearer, so that the disposable diaper itself can be shaped more like the shape of the body of a wearer.

(5) Other Embodiments

As described above, the present invention is disclosed through the above embodiments of the present invention. However, it should not be interpreted that the statements and drawings constituting a part of the present disclosure limit the present invention. From this disclosure, a variety of alternate embodiments, examples, and applicable techniques will become apparent to one skilled in the art.

Furthermore, in the above-described embodiment, the open-type disposable diaper provided with has been described as an example. However, the present invention can also be applied to a pant-type disposable diaper. In the pant-shaped diaper, which has a waistline opening and a pair of leg hole openings by joining together both right-left side edges of the exterior layer sheet making up the front waistline region and the rear waistline region, the exterior layer sheet in the front waistline region and the rear waistline region includes elastic elements which are contractible and extendable in the product widthwise direction W, and the disposable diaper is retained along the waistline of a wearer by contracting these elastic elements. That is, the range in which the right-left side edges extending in the product longitudinal direction L are joined together, functions as a waistline retaining unit. Furthermore, in the disposable diaper according to the modification, rather than leg gathers formed from an elastic nonwoven sheet, leg gathers formed from thread-like elastic members may be provided.

As described above, needless to say, the present invention includes various embodiments and the like not described here. Therefore, the technical range of the present invention is to be defined only by the inventive specific matter according to the adequate claims from the above description.

The entire contents of Japanese Patent Application No. 2012-082890(filed on Mar. 30, 2012) are incorporated in the present specification by reference.

INDUSTRIAL APPLICABILITY

It is possible to provide a disposable diaper configured that a length in the product widthwise direction of the absorber is made smaller in the crotch region as compared to the front waistline region, the disposable diaper which prevents the absorber arranged at the abdominal side from deforming in the widthwise direction to thereby prevent the leakage of bodily fluid or reduction of the fitting property.

The invention claimed is:
1. A disposable diaper, comprising:
    a front waistline region;
    a rear waistline region;
    a crotch region positioned between the front waistline region and the rear waistline region;
    a product longitudinal direction from the front waistline region towards the rear waistline region;
    a product widthwise direction perpendicular to the product longitudinal direction; and
    an absorber running across the crotch region and extending to the front waistline region and rear waistline region; and
    a waistline retaining unit that retains the disposable diaper around a body of a wearer, in the front waistline region and the rear waistline region;
wherein
    the absorber is provided with a narrow region that a length in the widthwise direction of the absorber becomes smaller towards an inner side in the product longitudinal direction;
    a length of the absorber in the crotch region in the product widthwise direction is smaller than a length of the absorber in the front waistline region and a length of the absorber the rear waistline region in the product widthwise direction;
    the absorber includes:
    a first region arranged at least partially in the crotch region;

a second region arranged adjacent to the first region at an outer side from the first region in the product longitudinal direction and having a lower bending rigidity than that of the first region; and a third region arranged adjacent to the second region at an outer side from the second region in the product longitudinal direction and having a higher bending rigidity than that of the second region;

a boundary between the first region and the second region is arranged at the side of the front waistline region from a center of the disposable diaper in the product longitudinal direction and is arranged in the narrow region;

a boundary between the second region and the third region is arranged at the side of the crotch region from an end at the crotch region side of the waistline retaining unit in the front waistline region; and an end at the front waistline region side of the third region is arranged at the side of the front waistline region from the end at the crotch region side of the waistline retaining unit in the front waistline region.

2. The disposable diaper according to claim 1, wherein a compressed unit having the absorber compressed in a product thickness direction is formed in at least the first region or the third region.

3. The disposable diaper according to claim 2, wherein a plurality of the compressed units are formed intermittently across an entirety of at least the first region or the third region.

4. The disposable diaper according to claim 1, wherein an end at the front waistline region side of the second region is arranged inside the narrow region.

5. The disposable diaper according to claim 1, further comprising a crotch stretch unit formed in an absorber arrangement region provided with the absorber, and configured to expand and contract in at least the product longitudinal direction.

6. The disposable diaper according to claim 5, wherein the absorber is further provided with a low rigidity unit that has no absorbent core making up the absorber or has a lower basis weight than that of other part, in a region at an outer side of the crotch stretch unit in the product longitudinal direction.

7. The disposable diaper according to claim 5, wherein the first region partially overlaps the crotch stretch unit in a product thickness direction.

8. The disposable diaper according to claim 1, wherein the second region is at a front side of the first region in the product longitudinal direction, and the third region is adjacent to the second region at a front side of the second region in the product longitudinal direction.

9. The disposable diaper according to claim 1, wherein the boundary between the first region and the second region and the boundary between the second region and the third region extend all the way across the absorber in the product width direction.

10. A disposable diaper, comprising:

a front waistline region;

a rear waistline region;

a crotch region between the front waistline region and the rear waistline region;

a product longitudinal direction from the front waistline region towards the rear waistline region;

a product widthwise direction perpendicular to the product longitudinal direction;

an absorber running across the crotch region and extending to the front waistline region and rear waistline region; and a waistline retaining unit configured to retain the disposable diaper around a body of a wearer, in the front waistline region and the rear waistline region;

wherein the absorber includes a narrow region, a dimension of the absorber in the narrow region in the product widthwise direction becomes smaller towards an inner side of the absorber in the product longitudinal direction, a dimension of the absorber in the crotch region in the product widthwise direction is smaller than a dimension of the absorber in the front waistline region in the product widthwise direction and a dimension of the absorber in the rear waistline region in the product widthwise direction, the absorber includes:
  a first region at least partially in the crotch region;
  a second region having a lower bending rigidity than that of the first region; and
  a third region having a higher bending rigidity than that of the second region, the second region is between the first region and the third region in the product longitudinal direction, a first boundary between the first region and the second region is in the front waistline region and the narrow region, a second boundary between the second region and the third region is in the front waistline region and closer to the crotch region than an end of a crotch region side of the waistline retaining unit in the front waistline region, the waistline retaining unit in the front waistline region includes opposite ends in the product longitudinal direction, and an end of a front waistline region side of the third region is between the opposite ends of the waistline retaining unit in the front waistline region in the product longitudinal direction.

* * * * *